US008986757B2

(12) United States Patent
Yang et al.

(10) Patent No.: US 8,986,757 B2
(45) Date of Patent: Mar. 24, 2015

(54) ESSENTIAL OILS INHIBIT MOLD ON WOOD

(75) Inventors: Vina W. Yang, Verona, WI (US); Carol A. Clausen, DeForest, WI (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 1279 days.

(21) Appl. No.: 12/163,497

(22) Filed: Jun. 27, 2008

(65) Prior Publication Data
US 2009/0017142 A1    Jan. 15, 2009

Related U.S. Application Data

(63) Continuation-in-part of application No. 11/716,429, filed on Mar. 9, 2007, now abandoned.

(60) Provisional application No. 60/782,576, filed on Mar. 15, 2006.

(51) Int. Cl.
*A61K 36/33*     (2006.01)
*A61K 36/537*    (2006.01)
*A61K 36/53*     (2006.01)
*A61K 36/185*    (2006.01)
*A61K 36/23*     (2006.01)

(52) U.S. Cl.
CPC ............... *A61K 36/53* (2013.01); *A61K 36/185* (2013.01); *A61K 36/23* (2013.01)
USPC ............ 424/745; 424/756; 424/768; 424/774

(58) Field of Classification Search
CPC ............................. A61K 36/33; A61K 36/537
USPC .................................. 424/745, 756, 768, 774
See application file for complete search history.

(56) References Cited

U.S. PATENT DOCUMENTS

| | | | |
|---|---|---|---|
| 3,968,301 A * | 7/1976 | Sears ........................... | 503/201 |
| 5,403,587 A | 4/1995 | Mccue | |
| 6,027,716 A | 2/2000 | Levin | |
| 6,858,317 B2 | 2/2005 | Aamodt | |
| 6,875,452 B1 | 4/2005 | Fyfe | |
| 6,890,960 B1 | 5/2005 | Henderson | |
| 6,897,244 B2 | 5/2005 | Zhu | |
| 2005/0013882 A1* | 1/2005 | Owen et al. ................... | 424/742 |
| 2005/0014730 A1 | 1/2005 | Carlson | |
| 2005/0019269 A1* | 1/2005 | Marks et al. .................... | 424/45 |
| 2006/0029630 A1 | 2/2006 | Overman | |
| 2006/0040847 A1 | 2/2006 | Weibel | |
| 2006/0134341 A1* | 6/2006 | Glassel et al. ................ | 427/440 |

OTHER PUBLICATIONS

Muanza DN et al., "Antibacterial and antifungal activities of nine medicinal plants from Zaire," Int. J. Pharmacog. 1994, 32:337-345.
Muanza DN et al., "Screening for antitumor and anti HIV activities of nine medicinal plants from Zaire," Int. J. Pharmacog. 1995, 33:98-106.
Cowan MM, "Plant products as antimicrobial agents," Clin. Microbiol. Rev., 1999, 12:564-582.
Hammer KA et al., "Antimicrobial activity of essential oils and other plant extracts," J. Appl. Microbiol., 1999, 86:985-990.
Hoffman BR et al., "Screening of antibacterial and antifungal activities of ten medicinal plants from Ghana," Pharmaceutical Biology, 2004, 42(1):13-17.
Mau JL et al., "Antimicrobial effect of extracts from Chinese chive, cinnamon and Corni fructus," J. Agric. Food. Chem., 2001, 49:183-188.
Sivropoulou A et al., "Antimicrobial activity of mint essential oil," J. Agric. Food Chem., 1995, 43:2384-2388.
Adam K et al., "Antifungal activities of *Origanum vulgare* subsp. *Mentha spicata, Lavandula angustifolia* and *Salvia fruiticosa* essential oil against human pathogenic fungi," J. Agric. Food Chem., 1998, 46:1739-1745.
Deferera DJ et al., "Analysis of essential oil from some Greek aromatic plants and their fungitoxicity on *Penicillium digitatum*," J. Agric. Food. Chem., 2000, 48:2576-2581.
Moretti et al., "In vivo activity of *Salvia officinalis* oil against *Botrytis cinera*," J. Essent. Oil Res., 1998, 10:157-160.
Muller-Riebau F et al., "Chemical composition and fungitoxic properties to phytopathogenic fungi of essential oil of selected aromatic plants growing wild in Turkey," J. Agric. Food. Chem., 1995, 43:2262-2266.
Rakotonirainy MS et al., "Screening for antifungal activity of essential oils and related compounds to control the biocontamination in libraries and archives storage areas," International Biodeterioration and Biodegradation, 2005, 55:141-147.
Scheffer TC et al., "Fungistatic vapors for control of mold in packages and equipment," Industrial and Engineering Chemistry, 1946, 38:619-621.
Sridhar SR et al., "Antifungal activity of some essential oils," J. Agric. Food. Chem., 2003, 512:7596-7599.

(Continued)

*Primary Examiner* — Chris R Tate
*Assistant Examiner* — Deborah Davis
(74) *Attorney, Agent, or Firm* — John D. Fado; Lesley D. Shaw; Janet I. Stockhausen

(57) ABSTRACT

Methods of treating wood lumber to inhibit growth of mold fungi by surface treating the wood lumber with an essential oil, diluted or undiluted, being geranium Egyptian, thyme, dill weed or rosemary. Various surface treatments include dipping, spraying, brushing and vapor exposure.

9 Claims, 3 Drawing Sheets

(56) References Cited

OTHER PUBLICATIONS

Wang S-Y et al., "Antifungal activities of essential oils and their constituents from indigenous cinnamon (*Cinnamomum osmophloeum*) leaves against wood decay fungi," Bioresource Technology, 2005, 96:813-818.

Edwards V, "The Aromatherapy Companion," 1999 Storey Brooks, Pownal, Vermont, pp. 55-62.

Schnaubelt K, "Advanced aromatherapy: The science of essential oil therapy," 1998 Healing Arts Press, Rochester, Vermont, pp. 9-41.

Maruzzella J C et al., "Action of Odoriferous Organic Chemicals and Essential Oils on Wood-Destroying Fungi," 1960 Plant Disease Reporter, 44:10 pp. 789-792.

Hill, Robert A, et al., "Use of Natural Products in Sapstain Control," 1997 Strategies for Improving Protection of Logs and Lumber, Rotorua, NZ, Nov. 21-22, 1997, pp. 39-42.

Inouye, M, et al., "Antisporulating and respiration-inhibitory effects of essential oils on filamentous fungi," 1998 Mycoses, 41, pp. 403-410.

Stranks, D M, "Essential Oils as Sapstain Fungicides," 1977 Bi-monthly research notes, 33:6, pp. 44-45.

Maruzzella, JC and Ligouri, L, "The in vitro antifungal activity of essential oils," 1958 J Am. Pharmaceutical Assoc, 47 pp. 250-254.

Maruzzella, JC and Sicurella, NA, "Antibacterial Activity of Essential Oil Vapors," 1960 J Am Pharmaceutical Assoc, 49 pp. 692-694.

Sivropoulou, A, et al., "Antimicrobial, cytotoxic and antiviral activities of *Salvia fruticosa* essential oil," 1997 J Agricult Food Chem, 45 pp. 3197-3201.

American Society for Testing and Material, 1998, Standard test method for fungicides for controlling sapstain and mold on unseasoned lumber (laboratory method). ASTM Standard D4445-91, West Conshohocken, PA, vol. 11.01, pp. 497-500.

American Society for Testing and Material, 1986. Standard test method for resistance to growth of mold on the surface of interior coatings in an environmental chamber. ASTM D3273-00, West Conshohocken, PA, vol. 06.01, pp. 411-413.

SAS V9.1.2, SAS/STAT 9.1 User's Guide, SAS Institute, Inc., Cary, NC, pp. 5136, 2004.

\* cited by examiner

ESSENTIAL OILS INHIBIT MOLD ON WOOD

PRIORITY INFORMATION

This application claims priority to U.S. Provisional Patent Application Ser. No. 60/782,576 filed Mar. 15, 2006, which is also incorporated herein by reference.

This application is a continuation-in-part of U.S. Nonprovisional patent application Ser. No. 11/716,429 filed Mar. 9, 2007 now abandoned, which is also incorporated herein by reference.

STATEMENT REGARDING FEDERALLY SPONSORED RESEARCH OR DEVELOPMENT

The U.S. Government has certain rights in the invention disclosed herein.

FIELD OF THE INVENTION

Methods of manufacture including treatment of untreated wood with essential oils for preventing, inhibiting or controlling growth of mold fungi. Methods of treatment include dip and vapor processes. Essential oils include dill weed, geranium Egyptian, rosemary and thyme.

BACKGROUND OF THE INVENTION

Moisture management remains the most important critical factor for controlling mold growth on wood and wood products during storage, construction and in service. Potential health risks caused by mold growth in houses and non-residential wooden structures have been a major concern for homeowners, building contractors and insurance companies alike. Law suits claiming health problems caused by indoor mold exposure exceeded 2.8 billion dollars in 2002.

Chemical fungicides commonly used to control the growth of mold on wood are not appropriate for many indoor applications. Natural alternatives that are user friendly and demonstrate low toxicity to humans are desirable for indoor applications. Essential oils are known for their natural, non-toxic components including monoterpenes, diterpenes, and hydrocarbons with various functional groups.

In the early 1990's, it was reported that bioactive plant extracts may be effective against bacteria and fungi. (See Muanza K et al., Antibacterial and antifungal activities of nine medicinal plants from Zaire, *Int. J. Pharmacog.* 32:337-345 (1994); and Muanza D N et al., Screening for antitumor and anti HIV activities of nine medicinal plants from Zaire, *Int. J. Pharmacog.* 33:98-106 (1995)). Antimicrobial and antifungal activities of essential oils in food applications, pharmaceutical research and other scientific areas have also been reported. (See Cowan M M, Plant products as antimicrobial agents, *Clin. Microbiol Rev.* 12:564-582 (1999); Hammer K A et al., Antimicrobial activity of essential oils and other plant extracts, *J. Appl. Microbiol.* 86:985-990 (1999); Hoffman B R et al., Screening of antibacterial and antifungal activities of ten medicinal plants from Ghana, *Pharmaceutical Biology* 42(1): 13-17 (2004); Mau J L et al., Antimicrobial effect of extracts from Chinese chive, cinnamon and *Corni fructus, J. Agric. Food. Chem.* 49:183-188 (2001); Sivropoulou A et al., Antimicrobial activity of mint essential oil, *J. Agric. Food Chem.* 43:2384-2388 (1995); Adam K et al., Antifungal activities of *Origanum vulgare* subsp. *Mentha spicata, Lavandula angustifolia* and *Salvia fruiticosa* essential oil against human pathogenic fungi, *J. Agric. Food Chem.* 46:1739-1745 (1998); Deferera D J et al., Analysis of essential oil from some Greek aromatic plants and their fungitoxicity on *Penicillium digitatum, J. Agric. Food. Chem.* 48:2576-2581 (2000); Moretti et al., In vivo activity of *Salvia officinalis* oil against *Botrytis cinera, J. Essent. Oil Res.* 10:157-160 (1998); Muller-Riebau F et al., Chemical composition and fungitoxic properties to phytopathogenic fungi of essential oil of selected aromatic plants growing wild in Turkey, *J. Agric. Food. Chem.* 43:2262-2266 (1995); Rakotonirainy M S et al., Screening for antifungal activity of essential oils and related compounds to control the biocontamination in libraries and archives storage areas, *International Biodeterioration ad Biodegradation* 55:141-147 (2005); Scheffer T C et al., Fungistatic vapors for control of mold in packages and equipment, *Industrial and Engineering Chemistry* 38:619-621 (1946); Sridhar S R et al., Antifungal activity of some essential oils, *J. Agric. Food. Chem.* 512:7596-7599 (2003); and Wang S-Y et al., Antifungal activities of essential oils and their constituents from indigenous cinnamon (*Cinnamomum osmophloeum*) leaves against wood decay fungi, *Bioresource Technology* 96:813-818 (2005)).

SUMMARY OF THE INVENTION

One aspect of the invention is a method of treating a cellulose-containing material to inhibit growth of mold fungi comprising the steps or acts of surface treating cellulose-containing material with a composition comprising in the range of greater than 10% volume to 100% volume thyme oil, and, in the range of 0% volume to less than 90% volume organic diluent.

In an exemplary embodiment of the method, the surface treating comprises dipping, low pressure spraying, high pressure spraying, brushing, misting, fogging, immersing, injecting or pressure treating the cellulose-containing material.

In another exemplary embodiment of the method, the organic diluent comprises an oil, an alcohol, a ketone or a mixture thereof.

In another exemplary embodiment of the method, the organic diluent comprises acetone, ethanol, vegetable oil, linseed oil or a mixture thereof.

In another exemplary embodiment of the method, the diluent comprises vegetable oil.

In another exemplary embodiment of the method, the composition comprises 12.5-100% volume thyme oil, and, 0-87.5% volume organic diluent.

In another exemplary embodiment of the method, the composition comprises 16.5-100% volume thyme oil, and, 0-83.5% volume organic diluent.

In another exemplary embodiment of the method, the composition comprises 20-100% volume thyme oil, and, 0-80% volume organic diluent.

In another exemplary embodiment of the method, the composition comprises 25-100% volume thyme oil, and, 0-75% volume organic diluent.

In another exemplary embodiment of the method, the composition comprises 100% volume thyme oil.

In another exemplary embodiment of the method, the cellulose-containing material comprises wood, wood product, wood lumber, oriented strandboard composite, engineered composite, drywall or ceiling tile.

Another aspect of the invention is a method of treating cellulose-containing material to inhibit growth of mold fungi comprising the steps or acts of vapor treating the cellulose-containing material with a composition comprising in the range of greater than 10% volume to 100% volume dill weed oil, rosemary oil or a mixture thereof, and, in the range of 0% volume to less than 90% volume organic diluent.

In an exemplary embodiment of the method, the method comprises passively vapor treating the cellulose-containing material.

In another exemplary embodiment of the method, the composition comprises 100% volume dill weed oil.

In another exemplary embodiment of the method, the composition comprises 100% volume rosemary oil.

In another exemplary embodiment of the method, the composition comprises 100% volume of a mixture of dill weed oil and rosemary oil.

In another exemplary embodiment of the method, the cellulose-containing material comprises wood, wood product, wood lumber, oriented strandboard composite, engineered composite, drywall or ceiling tile.

In another exemplary embodiment of the method, the organic diluent comprises an oil, an alcohol, a ketone or a mixture thereof.

In another exemplary embodiment of the method, the organic diluent comprises acetone, ethanol, vegetable oil, linseed oil or a mixture thereof.

In another exemplary embodiment of the method, the diluent comprises vegetable oil.

In another exemplary embodiment of the method, the composition comprises 12.5-100% volume dill weed oil, rosemary oil or a mixture thereof, and, 0-87.5% volume organic diluent.

In another exemplary embodiment of the method, the composition comprises 16.5-100% volume dill weed oil, rosemary oil or a mixture thereof, and, 0-83.5% volume organic diluent.

In another exemplary embodiment of the method, the composition comprises 20-100% volume dill weed oil, rosemary oil or a mixture thereof, and, 0-80% volume organic diluent.

In another exemplary embodiment of the method, the composition comprises 25-100% volume dill weed oil, rosemary oil or a mixture thereof, and, 0-75% volume organic diluent.

Another aspect of the invention is a method of treating a cellulose-containing material to inhibit growth of mold fungi comprising the steps or acts of surface treating cellulose-containing material with a composition comprising in the range of greater than 10% volume to 100% volume geranium Egyptian oil, and, in the range of 0% volume to less than 90% volume organic diluent.

In an exemplary embodiment of the method, the surface treating comprises dipping, low pressure spraying, high pressure spraying, brushing, misting, fogging, immersing, injecting or pressure treating the cellulose-containing material.

In another exemplary embodiment of the method, the organic diluent comprises an oil, an alcohol, a ketone or a mixture thereof.

In another exemplary embodiment of the method, the organic diluent comprises acetone, ethanol, vegetable oil, linseed oil or a mixture thereof.

In another exemplary embodiment of the method, the diluent comprises vegetable oil.

In another exemplary embodiment of the method, the composition comprises 12.5-100% volume geranium Egyptian oil, and, 0-87.5% volume organic diluent.

In another exemplary embodiment of the method, the composition comprises 16.5-100% volume geranium Egyptian oil, and, 0-83.5% volume organic diluent.

In another exemplary embodiment of the method, the composition comprises 20-100% volume geranium Egyptian oil, and, 0-80% volume organic diluent.

In another exemplary embodiment of the method, the composition comprises 25-100% volume geranium Egyptian oil, and, 0-75% volume organic diluent.

In another exemplary embodiment of the method, the composition comprises 100% volume geranium Egyptian oil.

In another exemplary embodiment of the method, the cellulose-containing material comprises wood, wood product, wood lumber, oriented strandboard composite, engineered composite, drywall or ceiling tile.

Another aspect of the invention is a method of treating wood or cellulose-containing material to inhibit growth of mold fungi comprising the steps or acts of surface treating the cellulose-containing material with an essential oil being geranium Egyptian, thyme or a combination thereof. In an exemplary embodiment, the surface treatment includes dipping, low pressure spraying, high pressure spraying, brushing, misting, fogging, immersing, injecting, pressure treating and other suitable methods of treating the surface of the cellulose-containing material. In another exemplary embodiment, the surface treatment includes dipping, low pressure spraying, high pressure spraying, brushing, misting, fogging, immersing, injecting, pressure treating and other suitable methods of treating the surface of the cellulose-containing material with geranium Egyptian. In another exemplary embodiment, the surface treatment includes dipping, spraying or brushing the cellulose-containing material with thyme.

Another aspect of the invention is a method of treating wood or cellulose-containing material to inhibit growth of mold fungi comprising the steps or acts of vapor treating the cellulose-containing material with an essential oil being dill weed, rosemary or a combination thereof. In an exemplary embodiment, the vapor treatment is passive vapor treatment, which may also be referred to as fumigating. The vapor treatment may also include other suitable methods of vapor treating the surface of the cellulose-containing material. In another exemplary embodiment, the cellulose-containing material is vapor treated with dill weed. In another exemplary embodiment, the cellulose-containing material is vapor treated with rosemary.

In an exemplary embodiment of any of the inventive methods herein, the cellulose-containing material may be any commercially-available or otherwise suitable materials, including wood (such as southern yellow pine), wood products such as wood lumber, engineered composite such as oriented strandboard ("OSB") composite, engineered composite, paper coated products such as drywall, or ceiling tile.

In another exemplary embodiment of any of the methods, the mold fungi may be any commonly found mold fungi, such as *Trichoderma viride, Aspergillus niger, Penicillium chrysogenum* or combinations thereof.

DETAILED DESCRIPTION OF EXEMPLARY EMBODIMENTS

Figure 1:
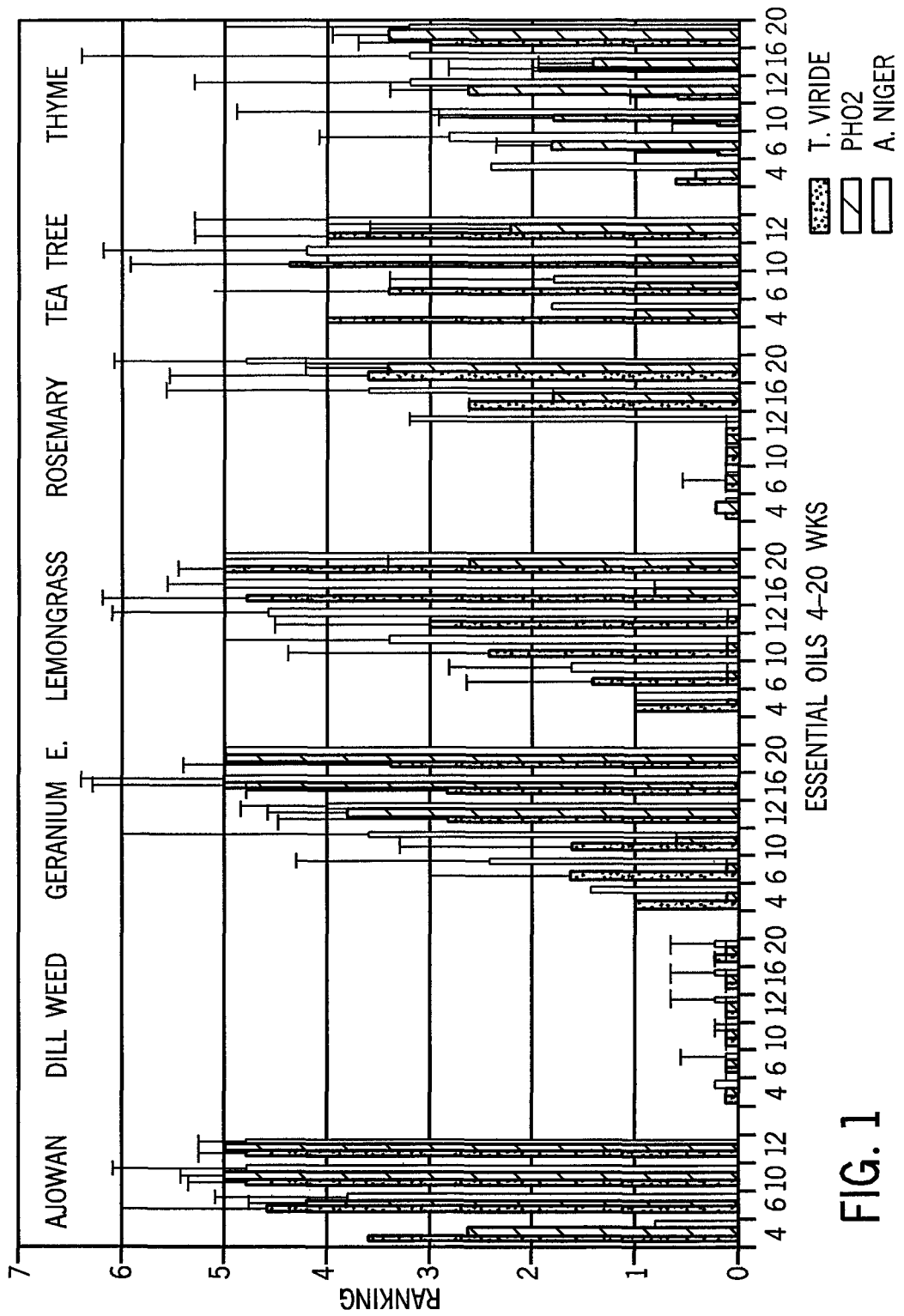
FIG. 1 shows a bar graph comparing seven different essential oils against mold fungi growth using the vapor method of treatment on SYP, whereby the analysis included mold resistance of SYP specimens exposed to vapors of seven essential oils (each alone) and challenged with three mold fungi individually in a Petri dish test chamber.

Seven essential oils were tested. The essential oils included ajowan, dill weed, geranium Egyptian, lemongrass, rosemary, tea tree and thyme. The oils were obtained from New Directions Aromatics Inc., San Francisco, Calif. All oils were used at full strength unless specified otherwise. Major components and functional groups of the tested oils are found in Edwards V, *The Aromatherapy Companion*, Published by Storey Brooks, Pownal, Vt., pp. 55-62; and Schnaubelt K, *Advanced aromatherapy: The science of essential oil therapy*, Published by Healing Arts Press, Rochester, Vt., pp. 9-41, which are hereby incorporated by reference.

Fungal strains. Three types of mold fungi were grown on 2% malt agar (Difco, Becton Dickinson & Co., Sparks, Md.): *Aspergillus niger* 2.242 (provided by University of Virginia), *Penicillium chrysogenum* PH02 (from Forest Product Laboratory, Madison, Wis.), and *Trichoderma viride* ATCC 20476. *Aureobasidium pullulans* was grown on 2% potato dextrose agar (Difco) for 2 weeks explicitly for inoculation of the soil in the tank test chamber. Spore suspensions of remaining test fungi were prepared by washing the surface of each malt agar plate with 10-15 ml of sterile deionized water (DI) according to ASTM standard D4445-91 (ASTM 1998). In one set of tests, a mixture of 3 mold spore suspensions was transferred to a spray bottle and diluted to 100 ml with DI water to yield $3 \times 10^7$ spores/ml. Spores of individual mold strains were prepared the same as described above for subsequent tests on individual test fungi. The spray bottle was adjusted to deliver 1 ml inoculum per spray.

Test Specimens. Southern yellow pine (SYP) specimens (7×20 mm cross section by 7 cm long), cut from southern pine mill ends obtained from a Mississippi sawmill and stored at 0° C. were used in the petri dish chamber method. Test specimens of kiln-dried SYP, cut into a series of 75×100 mm (12.5 mm thick) samples were used in the tank test chamber method.

Dip stake treatment. Five random replicate specimens were dip-treated for 15 seconds in various essential oils. Vegetable oil served as the control. Specimens were held in a closed container overnight at room temperature according to ASTM test methods D4445-91 and D3273-00 (ASTM 1998; 1986) prior to inoculation with spores of the test fungi. Additionally, thyme and tea tree oil dilutions of 1:2, 1:4 and 1:8 were tested individually and in combination for mold resistance for 22 weeks.

Vapor exposure treatment. Five untreated specimens were held overnight at room temperature in a closed glass Petri dish (150×250 mm). A small glass dish (4 cm diameter) containing an individual test oil was set beside the specimens prior to inoculation with spores of the test fungi. Vegetable oil served as the control.

Petri dish test chamber. Each Petri dish test chamber (150× 25 mm) (B-D Falcon, Los Angeles, Calif.) contained four layers of blotting paper that was saturated with 30 ml DI water and covered with a polyethylene mesh spacer to elevate specimens. Specimens were sprayed with 1 ml of mixed or individual mold spore inoculum 24 hr post-treatment with essential oil. Petri dish test chambers were sealed in polyethylene bags to prevent drying and incubated at 27° C., 70% RH. Specimens were evaluated for mold growth at 4, 6, 10, 12, 16, and 22 week marks and rated on a scale of 0 to 5:0 indicating no growth and 5 indicating heavy mold growth. Specimen rating ceased when test oils failed to subsequently inhibit growth of test fungi.

Tank test chamber. A self-contained stainless steel environmental chamber (28×20×26 mm) containing water, soil and hangers for suspending test samples was covered with a pitched roof to prevent condensation from dripping onto specimens. Test chambers were set up in a conditioning room at 30° C. and 70% RH. This set-up, a modification of ASTM D3273-00 (ASTM 1986), is a test method for resistance to mold growth on the surface of Interior Coatings in an Environmental Chamber which did not include an internal heater, electrical fan, or water circulator.

Non-sterile top soil was placed in a tray to a depth of 1 inch above the water level. Soil was inoculated with mold spores from three fungi, *Aureobasidium pullulans*, *Aspergillus niger* and *Penicillium chrysogenum*, two weeks before placing the test specimens in the chamber. Test specimens were vertically suspended across the width of the chamber over inoculated soil.

Specimens individually dip-treated with thyme or geranium Egyptian oils were inoculated with a mixed spore suspension 24 hr post-treatment. For the vapor exposure method, a glass Petri dish containing 5 ml dill weed oil was placed on the soil surface for 24 hours before untreated specimens were introduced.

Figure 2:
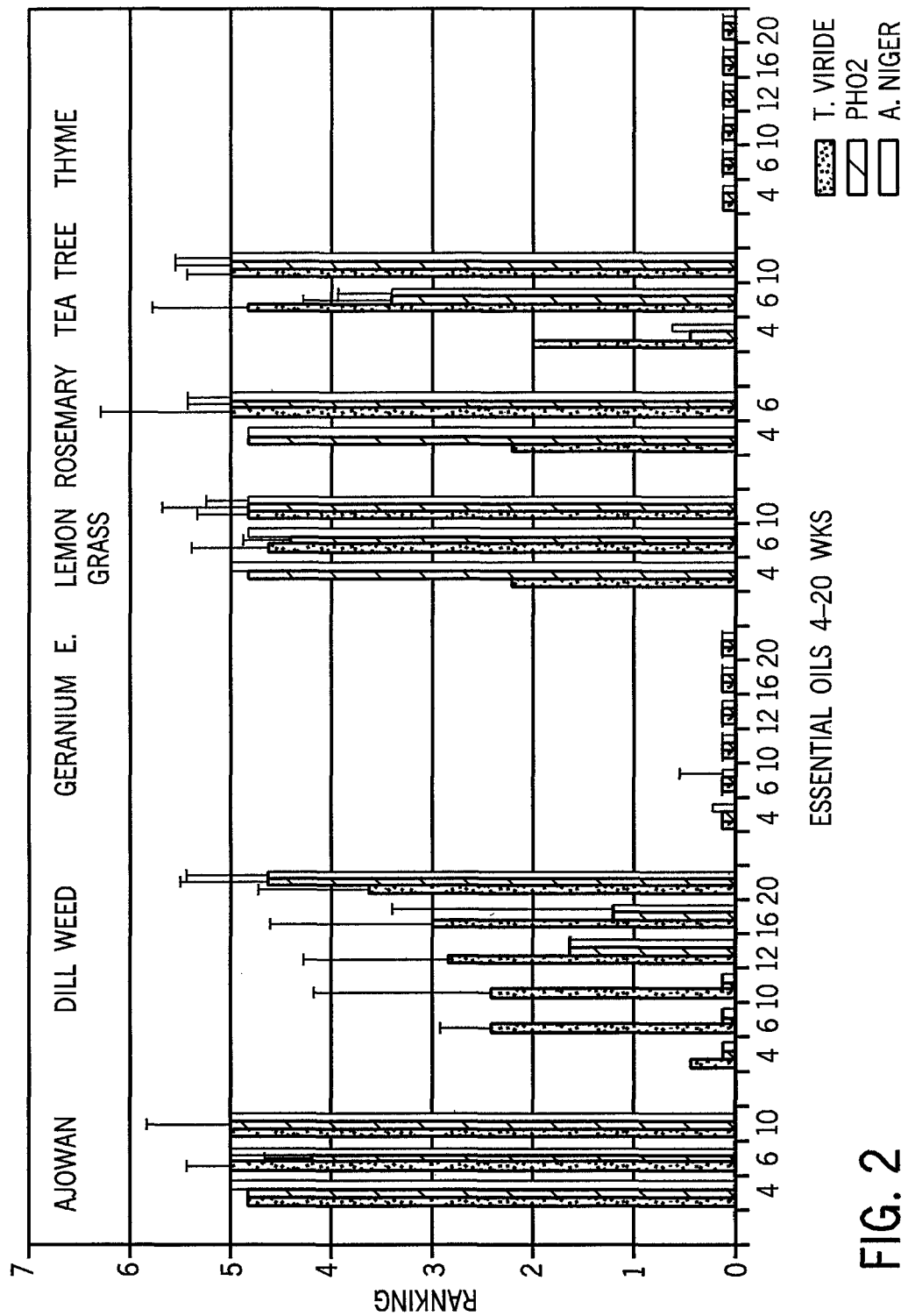
FIG. 2 shows a bar graph comparing seven different essential oils against mold fungi growth using the dip stake method of treatment on southern yellow pine (SYP), whereby the analysis included mold resistance of SYP specimens individually dip-treated with seven essential oils (each alone) and challenged with three mold fungi individually in a Petri dish test chamber.

Essential oils were evaluated for antifungal effects on wood against three common air borne mold fungi. The essential oils were assessed using two different methods of treatment: vapor exposure and dip stake. The results are shown in FIGS. 1 and 2, respectively.

Dip stake results. Specimens were initially rated after 4 weeks incubation. Ratings continued periodically through 20 weeks incubation or until test oils failed to substantially inhibit test fungi. Results of the dip stake method showed that ajowan, lemongrass, rosemary and tea tree were about 80% covered with mold growth at week 6 and 100% covered at week 10. The inhibitory effect on the surface of wood specimens was low for ajowan, lemongrass, rosemary and tea tree using the dip stake method of treatment.

In contrast, dill weed oil showed protection against *P. chrysogenum* PH02 and *A. niger*, but not against *T. viride*, for up to 10 weeks. Surprisingly, geranium Egyptian and thyme completely inhibited all test fungi for at least 20 weeks (rated 0 for mold growth). Control stakes dipped in the vegetable oil control showed 100% mold coverage at week 4. Diluted thyme oil (1:8) showed no mold growth up to 22 weeks, while a 1:2 dilution of tea tree oil only demonstrated mold inhibition for 6 weeks. The combination of thyme and tea tree oils was less inhibitory than thyme alone.

Vapor exposure results. Test fungi showed a different response to vapor exposure of essential oils. The most effective mold inhibitor was dill weed vapor. It retarded growth of all three molds for at least 20 weeks. Rosemary vapor inhibited *T. viride* and *Penicillium* for 12 weeks and *A. niger* for 10 weeks (see FIG. 1). These findings may suggest that ketone volatilization likely plays a key role in preventing spore germination for dill weed and rosemary oils. Lemongrass vapor retarded *Penicillium* growth for 12 weeks, but was ineffective against the other two test mold fungi. Ajowan and tea tree vapors did not inhibit mold fungi. Contrary to dip treatment results, geranium Egyptian and thyme oil vapors did not inhibit mold fungi under the conditions used, which may suggest that the monoterpene components either inhibit spore germination or vegetative growth upon contact.

Petri dish test chamber versus Tank test chamber. Both dip treatment and vapor exposure in the tank test chamber experiment showed positive inhibition for all test fungi on treated specimens for at least 8 weeks. Overall, test results were comparable for the two test apparatuses used.

An important and unexpected observation was that the antifungal properties of thyme and geranium Egyptian oils play an important role in wood protection from mold fungi. The active components of thyme oil (namely geraniol, thymol and carvone) provided significant inhibition of mold growth and serve as a broad spectrum biocide against commonly occurring molds. (See Scheffer T C, 1946). Ajowan was ineffective at inhibiting mold under the conditions used, which is surprisingly contrary to the results reported in Sridhar et al., 2003.

Thyme and geranium Egyptian inhibited mold spores using the dip stake method of treatment.

A statistical evaluation was conducted to model the minimum effective fungicidal concentration ($MFC_{90}$) that provides at least 90% probability of a 0 rating for mold growth, which is an acceptable standard. Using SAS V9.1.2 available from SAS Institute, Inc., Cary, N.C. (SAS/STAT 9.1 User's Guide, SAS Publishing, pp. 5136, 2004), individual mold ratings for specimens treated at various thyme oil concentrations were evaluated and modeled as ordinal responses in cumulative complementary log-log models, which also modeled the probability of ratings as functions of the logarithm of fungicidal concentrations. The following thyme oil concentrations were tested: 6.67%, 10%, 12.5% and 20%. The $MFC_{90}$ of thyme oil was estimated at 16.5% (1:6.03) by that method.

Figure 3:
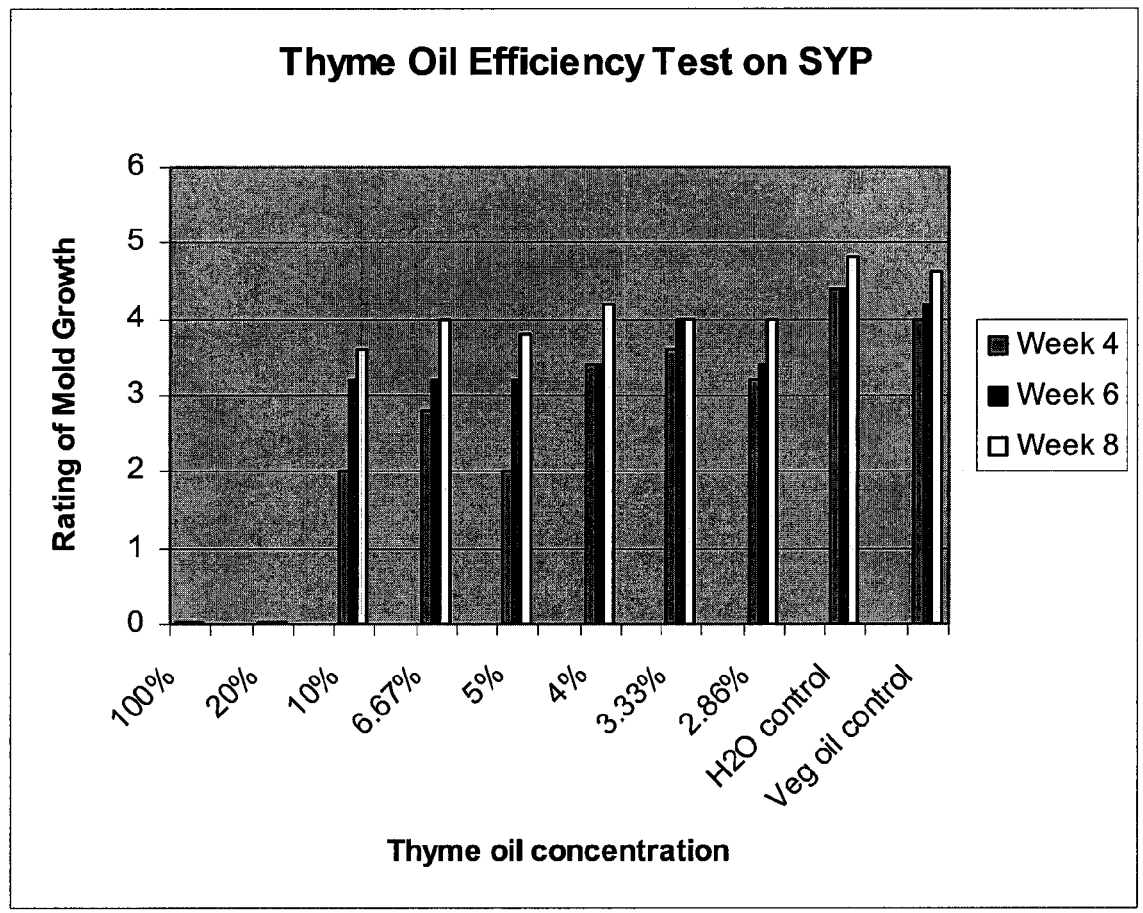
FIG. 3 demonstrates the effective inhibitory concentration of thyme oil against mold growth, whereby the experiment conducted at a dilution ratio of 1:10 (i.e. 10%) thyme oil with vegetable oil some mold inhibition occurred, and, whereby the experiment conducted at a dilution ratio of 1:8 (i.e., 12.5%) thyme oil showed no mold growth. Thus, treatment using a 1:10 solution of thyme oil diluted with an organic diluent is the point at which mold inhibition occurs, and treatment using a solution of less diluted thyme oil yields no mold growth for up to 8 weeks under the conditions set forth in the experimental. (Rating system: 0=no mold growth, 1=20% mold growth, 2=40% mold growth, 3=60% mold growth, 4=80% mold growth, and 5=100% mold coverage on the wood surface).

In the ASTM standard laboratory test D4445-91, 12.5% (i.e., 1:8 dilution) thyme oil on southern yellow pine (SYP) consistently inhibited 100% mold growth for 8 weeks. The 10% (i.e., 1:10 dilution) inhibited/yielded 28% mold growth (average rating of 3.6) in the same laboratory experimental method (FIG. 3). Thus, based upon the empirical data, a reasonable extrapolation suggests that the minimum effective concentration of thyme oil necessary to provide complete protection from mold growth on the surface of SYP is less than 12.5% and greater than 10%.

The tendency for high volatilization is advantageous for broadening the range of useful application of essential oils to inhibit mold growth. Vapor inhibition of molds can advantageously provide protection for large volumes of wood products in a closed environment. Dill weed and rosemary oil vapors inhibited mold spores using the vapor exposure method of treatment.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements included within the spirit and scope of the invention, as set forth by the appended claims. The entire disclosures of all references, applications, patents, and publications cited above are hereby incorporated by reference.

We claim:

1. A method of preventing growth of mold fungi on cellulose-containing material, the method consisting of:
   applying a single treatment of a composition consisting of:
      at least 10% volume thyme oil, and,
      at least 10% volume organic diluents, wherein the organic diluents comprises acetone, ethanol, vegetable oil, linseed oil or a mixture thereof,
   to the surface of a cellulose-containing material, wherein the growth of mold fungi on the cellulose-containing material is prevented.

2. The method of claim 1, wherein the surface treating comprises dipping, low pressure spraying, high pressure spraying, brushing, immersing, injecting or pressure treating the cellulose-containing material.

3. The method of claim 1, wherein the diluent comprises vegetable oil.

4. The method of claim 1, wherein the composition consists of:
   12.5-90% volume of said thyme oil, and,
   up to 87.5% volume organic diluent.

5. The method of claim 1, wherein the composition consists of:
   16.5-90% volume of said thyme oil, and,
   up to 83.5% volume organic diluent.

6. The method of claim 1, wherein the composition consists of:
   20-90% volume of said thyme oil, and,
   up to 80% volume organic diluent.

7. The method of claim 1, wherein the composition consists of:
   25-90% volume of said thyme oil, and,
   up to 75% volume organic diluent.

8. The method of claim 1, wherein the composition comprises 90% volume of said thyme oil.

9. The method of claim 1, wherein the cellulose-containing material comprises wood, wood product, wood lumber, oriented strandboard composite, engineered composite, drywall or ceiling tile.

* * * * *